United States Patent [19]
Fishman et al.

[11] Patent Number: 5,097,810
[45] Date of Patent: Mar. 24, 1992

[54] ALLERGY TESTING APPARATUS AND METHOD

[75] Inventors: Henry Fishman, 5173 Linnean Terr. NW., Washington, D.C. 20008; Gary D. Johnson, New York, N.Y.; Jeffrey G. Smith, Arlington, Va.; Leonard Holtz, Oceanside, N.Y.

[73] Assignee: Henry Fishman, Washington, D.C.

[21] Appl. No.: 506,606

[22] Filed: Apr. 6, 1990

[51] Int. Cl.$^5$ ............................................. A61B 5/00
[52] U.S. Cl. ..................................... 128/743; 604/47; 604/191; 604/201
[58] Field of Search .................... 128/743; 604/46, 47, 604/181, 191, 201, 244, 411, 413

[56] References Cited

U.S. PATENT DOCUMENTS

| | | | |
|---|---|---|---|
| 3,289,670 | 12/1966 | Krug et al. | 604/47 |
| 3,556,080 | 1/1971 | Hein | 128/743 |
| 4,168,701 | 9/1979 | Chiulli | 128/655 |
| 4,292,979 | 10/1981 | Inglefield, Jr. et al. | 128/743 |
| 4,453,926 | 6/1984 | Galy | 604/47 |
| 4,711,247 | 12/1987 | Fishman | 604/47 |
| 5,027,826 | 7/1991 | Fishman | 604/47 |

Primary Examiner—Stephen C. Pellegrino
Assistant Examiner—Michael Rafa
Attorney, Agent, or Firm—Frishauf, Holtz, Goodman & Woodward

[57] ABSTRACT

An allergy testing apparatus for testing a patient for a plurality of allergies at the same time comprises an actuating member resiliently suspended from a frame member and which is movable relative to the frame member. A plurality of spaced apart substance sources are mounted in the frame member below the actuating member. A plurality of spaced apart needles or the like are mounted on the actuating member and extend in the same direction so as to pierce the respective substance sources during movement of the actuating member toward the skin of a patient to apply the substances to the skin of a patient. According to another feature of the invention, the device is shaped like a rotatable, drum-like device, having a plurality of layers. The needles or the like are covered over by a resilient layer, and substance containing means are mounted over the resilient layer and in registration with the respective needles. When the device is pressed against the skin of a patient, the resilient layer compresses, permitting the needles to pierce the substance containers to apply the substances to the skin of a patient. Adjustable length substance carrying means are also disclosed.

27 Claims, 7 Drawing Sheets

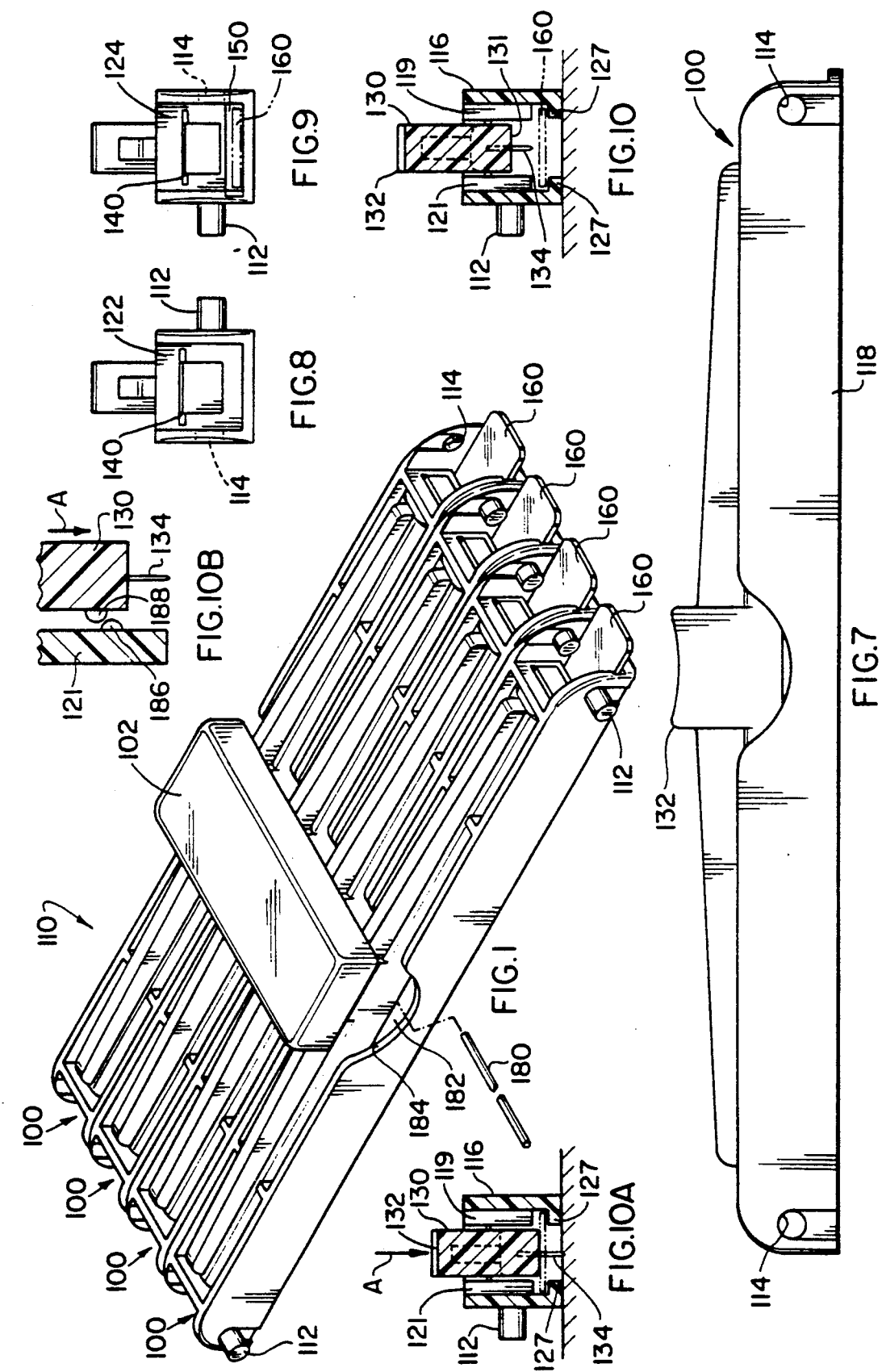

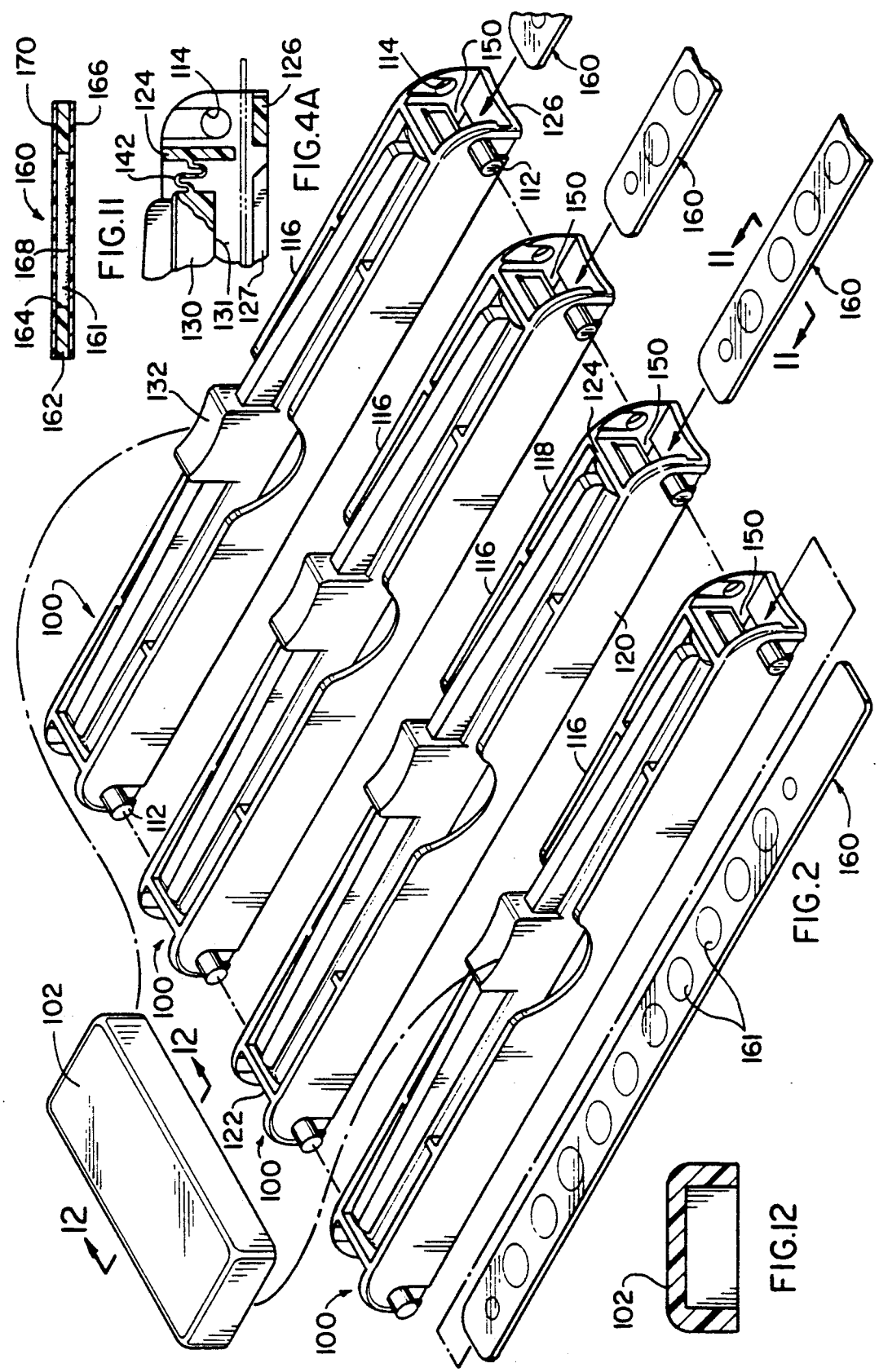

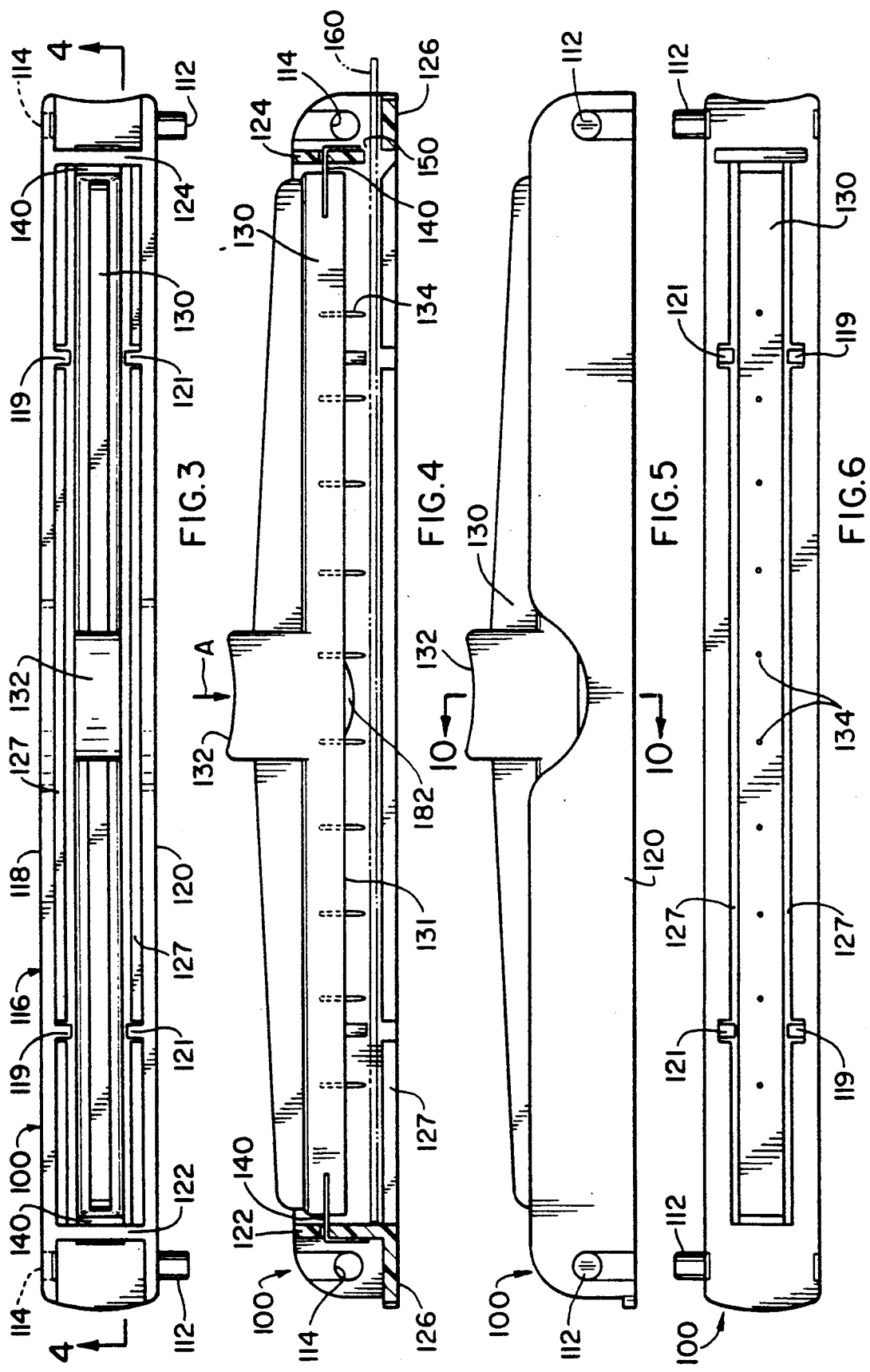

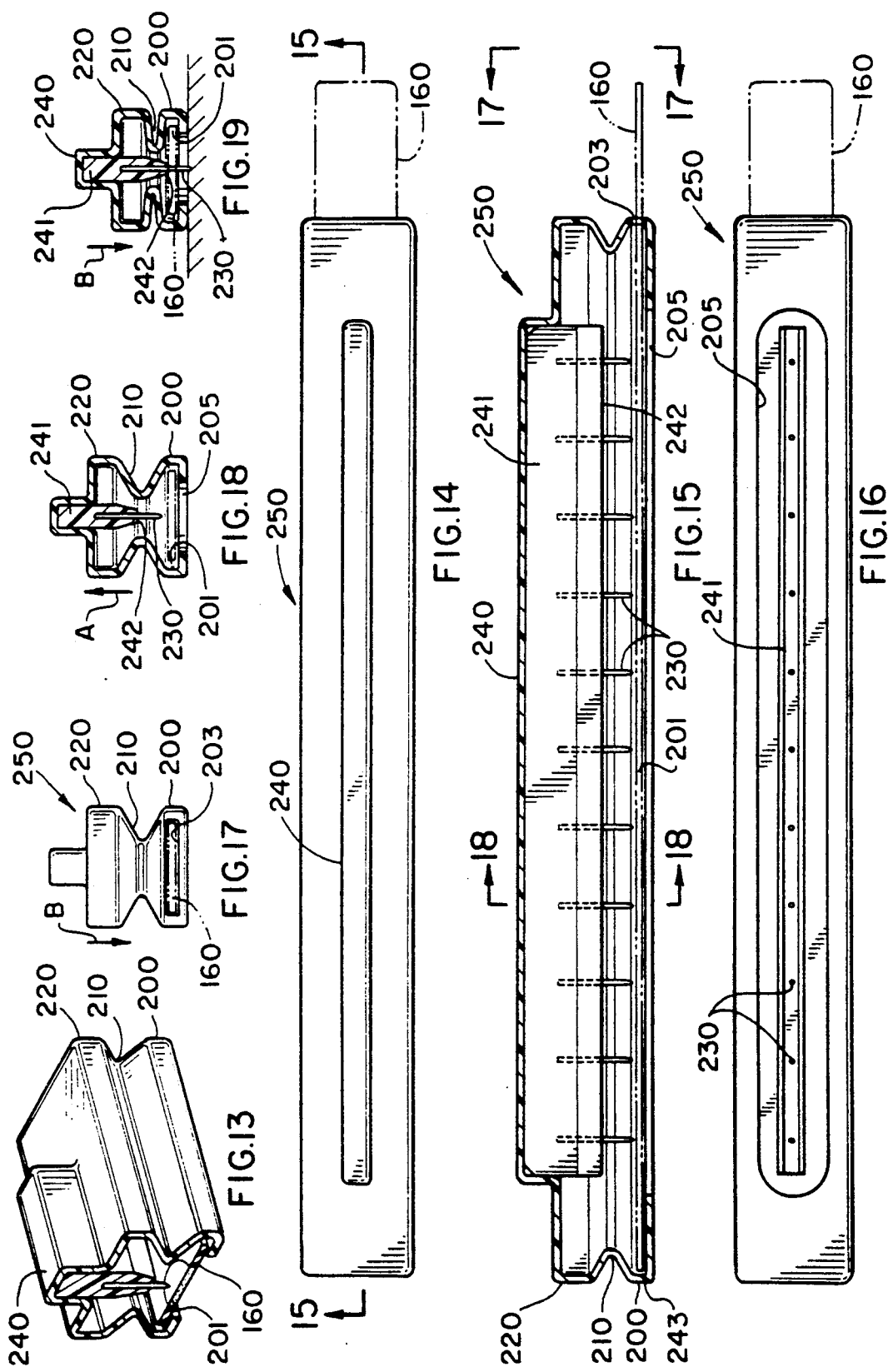

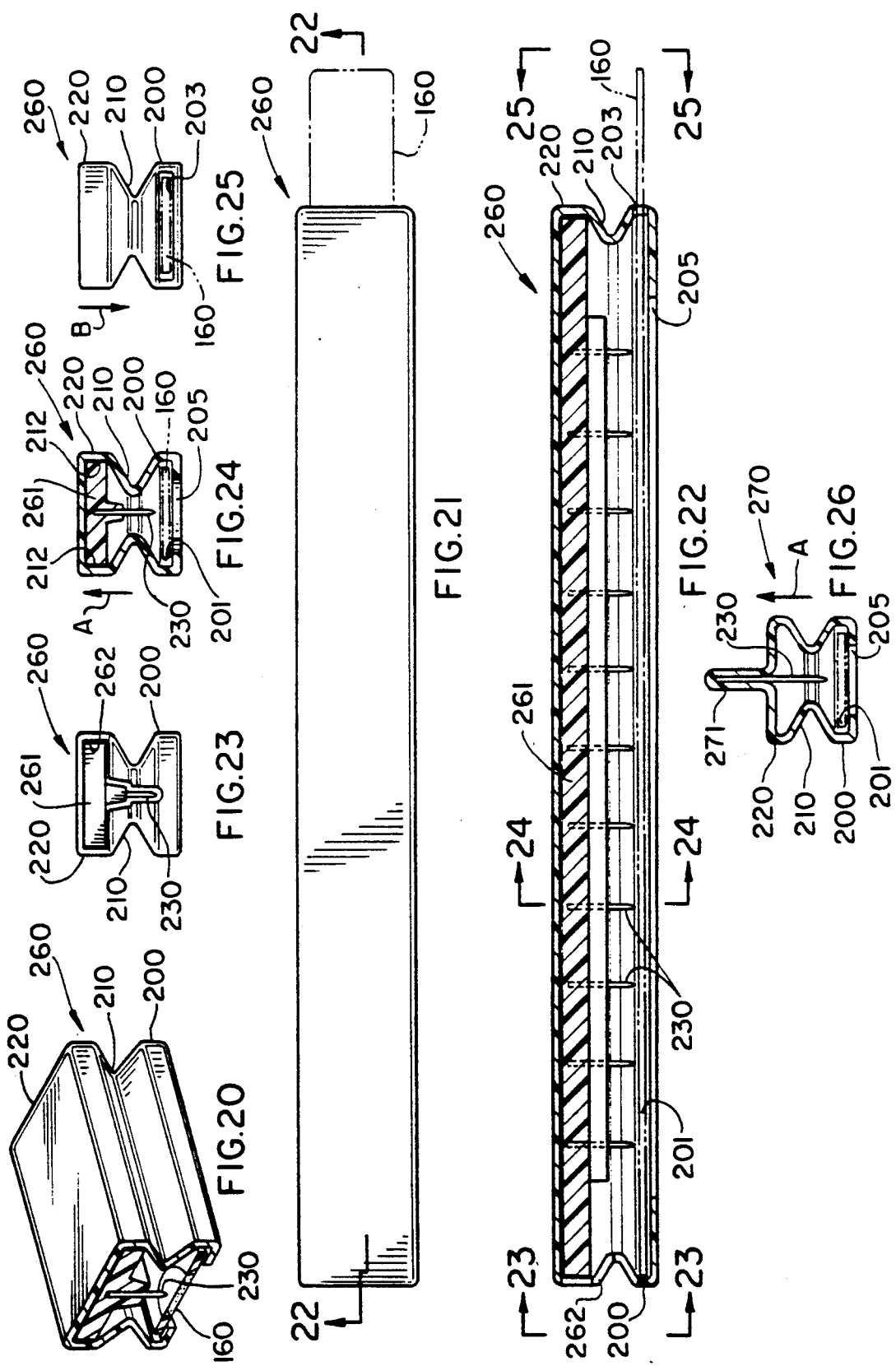

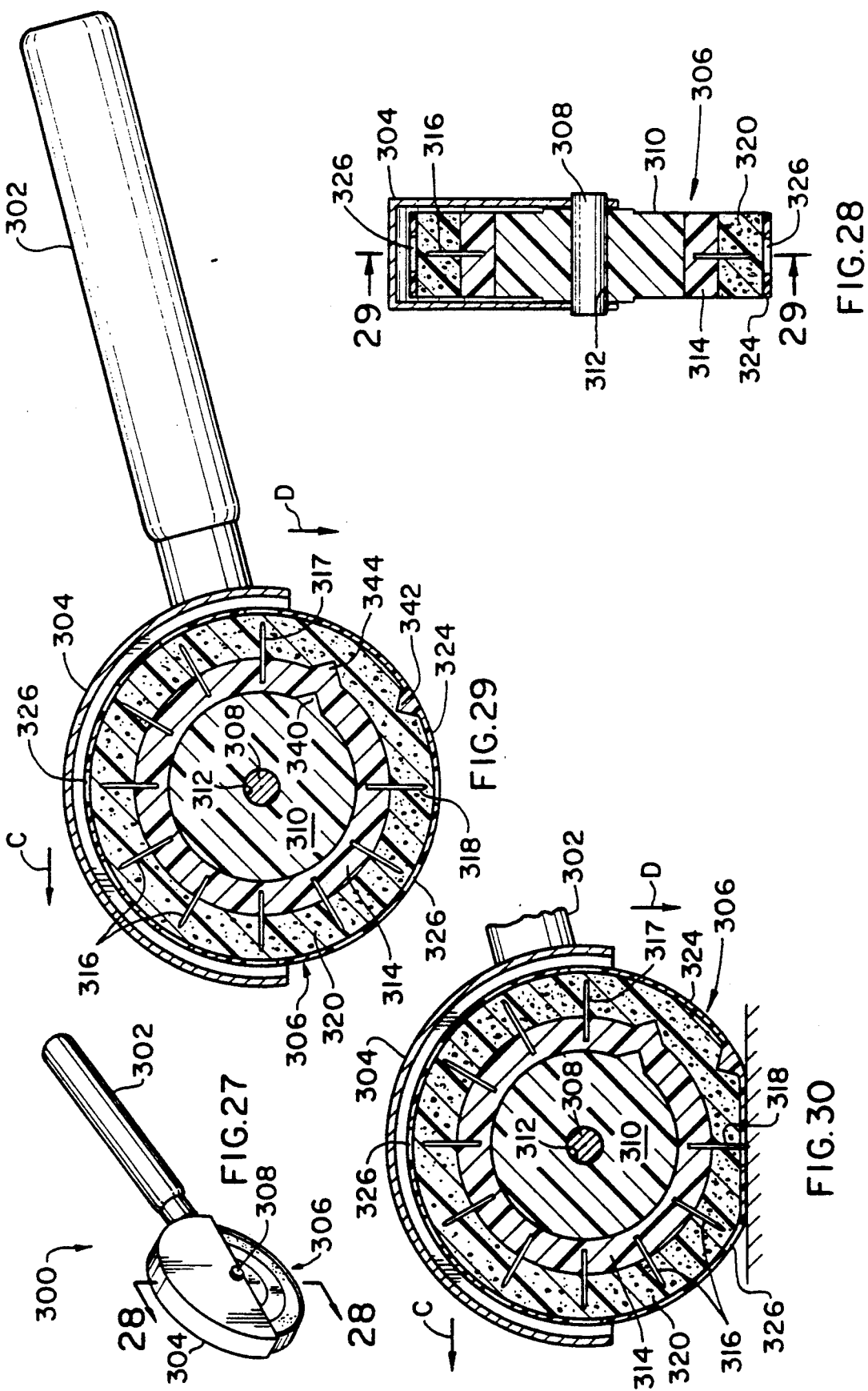

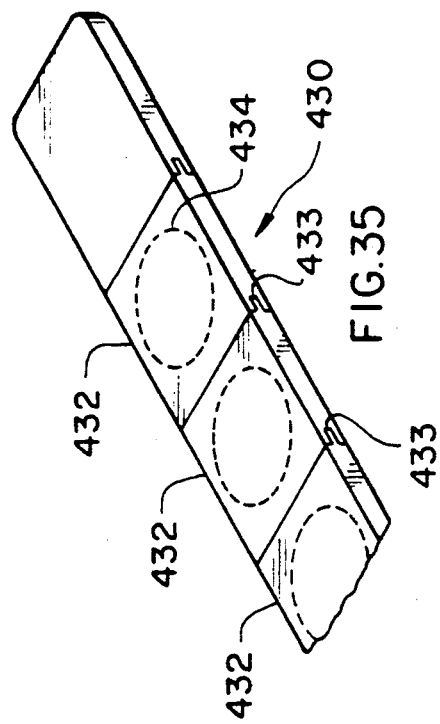
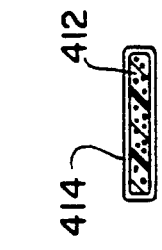
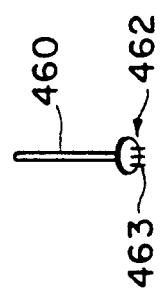
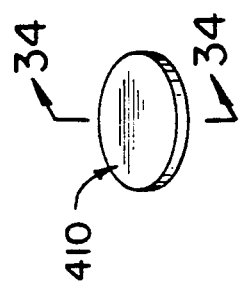
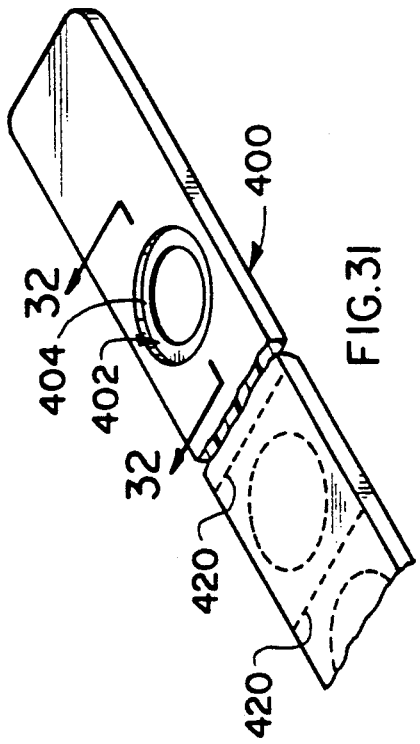

ALLERGY TESTING APPARATUS AND METHOD

CROSS REFERENCE TO RELATED PATENTS AND APPLICATIONS

This is an improvement of my prior device shown in U.S. Pat. No. 4,711,247, issued Dec. 8, 1987 and that disclosed in U.S. application Ser. Nos. 07/113,364, filed Oct. 21, 1987 and Ser. No. 07/339,863, filed Apr. 14, 1989.

BACKGROUND OF THE INVENTION

This invention relates to allergy testing methods and apparatuses, and more specifically to improved methods and apparatuses for testing a patient for a plurality of allergies at substantially the same time.

Allergy testing generally involves giving a patient a plurality of "prick or scratch" tests. Each prick or scratch test (hereinafter referred to as "test") is applied in order to determine whether or not a patient is allergic to a particular substance, such as pollen, animal dander, dust, foods, etc. A conventional test involves placing a drop of a test substance on the patient's skin and then using a needle to scratch the substance through the skin into a superficial layer of the skin. If a reaction occurs, the patient is generally considered to be allergic to the particular substance. Alternatively, allergy testing involves giving a patient a plurality of "intradermal" tests. Intradermal tests involve placing a small amount of a test substance into the dermis or deep skin layers, either by injection or puncture.

At present, allergy testing is carried out on an individual basis. Each test substance is dropped, one drop at a time, on the patient's arm or back. Each drop is then individually pricked through the skin with a separate needle. Alternatively, each individual substance is injected or punctured into the intradermal or deep skin layer. Either process is a very time consuming process (for both the patient and the practitioner) and very often involves multiple office visits for the patient. This leads also to a substantial amount of patient discomfort, expense and inconvenience.

The apparatus disclosed in U.S. Pat. No. 4,711,247 automates the above procedure and provides a means and method for testing a patient for a number of substances substantially at the same time. However, the apparatus of U.S. Pat. No. 4,711,247 is relatively bulky and complex.

The method and apparatus of Ser. No. 07/113,364, filed Oct. 21, 1987, of which the present inventor is a co-inventor, is improved with respect to complexity and cost, but still has the disadvantage that it is relatively bulky and requires individual packages of allergens.

An object of the present invention is to provide improved apparatuses and methods for testing patients for allergic reactions to a plurality of substances, all at substantially the same time. The invention will reduce the time required for testing, minimize patient discomfort, expense and inconvenience, and improve productivity.

A further object of the invention is to provide improved methods and apparatuses which will enable the plurality of allergy tests to be applied simultaneously without requiring a great deal of technical skill on the part of the operator.

Yet another object of the invention is to provide improved apparatuses which use pre-packaged allergens which are easily insertable in and removable from the apparatus, thereby facilitating loading the allergens, and improving the sterility of the apparatus.

Still another object of the invention is to provide an allergy testing system where the pricking or scratching or puncturing of the skin is always done to a given skin penetration depth which is predictable and which is replicable without requiring highly skilled operators.

Yet another object of the invention is to provide a simplified device which can be more easily manufactured by molding at a relatively low cost, and which is either re-usable or disposable.

Still another object of the invention is to provide such an allergy testing system wherein allergy testing sections, each carrying a plurality of allergens for testing, can be interconnected together in a simplified manner, so as to increase the number and variety of simultaneous allergen tests applied to the patient.

SUMMARY OF THE INVENTION

According to the present invention, an allergy testing apparatus for testing a patient for a plurality of allergies at substantially the same time comprises a frame member; an actuating member resiliently suspended from said frame member by suspending means; actuating means on said actuating member for moving said suspended actuating member relative to aid frame member; a plurality of spaced apart substance sources mounted in said frame member below said actuating member for carrying respective substances which are to be applied to the skin of a patient for testing; and a plurality of spaced apart pricking or piercing means on said actuating member and extending in substantially the same direction, each pricking or piercing means being associated with a respective substance source, said pricking or piercing means being movable from an inactive position out of contact with the skin of a patient to an active position for pricking or piercing the skin of a patient and applying an associated substance from said respective substance source to the skin of the patient when moved from said inactive position to said active position; said actuating member being movable relative to said frame member against the resiliency of said resilient suspending means for moving said plurality of pricking or piercing means from said inactive position to said active position to contact said substances contained in said plurality of spaced apart substance sources, respectively, and to apply the respective substances to the pricked or pierced skin of the patient at substantially the same time with said substances being spaced apart on the skin of said patient.

According to another aspect of the invention, an allergy testing apparatus for testing a patient for a rotatable, drum-like member; a plurality of spaced apart pricking or piercing means coupled to said drum member and extending substantially radially of said drum member and being spaced apart relative to each other over a circumferential portion of said drum member; resilient means over said pricking or piercing means for at least partially covering said piercing or pricking means; substance containing means mounted over said resilient means and including a plurality of substance sources spaced from each other and in registration with respective pricking or piercing means; and operating means coupled to said rotatable drum-like member for applying said rotatable drum-like member against the skin of a patient and for pressing said rotatable drum-like member in the direction of said skin of said patient to compress said resilient layer to thereby cause said pricking or piercing means to extend through said resilient layer and to pass through said respective substance sources so as to contact a respective substance and then pierce or prick the skin of a patient, thereby applying the substance in registration with the respective pricking or piercing means to the skin of a patient, and for rolling said drum-like member along the skin of a patient to sequentially apply substances to the skin of the patient at spaced apart locations on the skin of the patient by respective pricking or piercing means, as said drum-like member is rolled along the skin of the patient.

BRIEF DESCRIPTION OF THE DRAWINGS

FIG. 1 is a perspective view of one embodiment of an allergy testing apparatus of the present invention;

FIG. 2 is a perspective view thereof in a disassembled state, showing a number of allergy testing sections and how they interconnect to form the assembled embodiment of FIG. 1;

FIG. 3 is a top view of one of the testing sections shown in FIG. 2;

FIG. 4 is a cross-sectional view taken along line 4—4 in FIG. 3;

FIG. 4A is an abbreviated part-sectional view, similar to FIG. 4, showing an alternate method of suspending the bar member of the present invention;

FIG. 5 is a front view of the testing section shown in FIG. 3;

FIG. 6 is a bottom plan view of the testing section shown in FIG. 3;

FIG. 7 is a rear view of the testing section shown in FIG. 3;

FIG. 8 is a left end view of the testing section shown in FIG. 3;

FIG. 9 is a right end view of the testing section shown in FIG. 3;

FIG. 10 is a cross-sectional view of the testing section shown in FIG. 5, taken along line 10—10 in view FIG. 5, and shown mounted on the skin of a patient;

FIG. 10A is a cross-sectional view similar to that of FIG. 10, but showing the device in the operative position wherein the needles thereof are piercing or pricking the skin of a patient;

FIG. 10B is an enlarged fragmentary view similar to FIG. 10A, but showing a means for maintaining a needle carrying member in the "up" or inoperative position during non-use;

FIG. 11 is a cross-sectional view taken along the line 11—11 in FIG. 2, showing the construction of an allergy carrying member of the present invention; and FIG. 12 is a cross-sectional view of the actuating member shown in FIG. 2, taken along the line 12—12 in FIG. 2;

FIG. 13 is a partial, broken away perspective view of the first variation of the second embodiment of the present invention;

FIG. 14 is a full plan view of the device shown in FIG. 13;

FIG. 15 is a cross-sectional view per line 15—15 taken in FIG. 14;

FIG. 16 is a bottom view common to all three variations of the second embodiment;

FIG. 17 is a right end view per line 17—17 taken in FIG. 15;

FIG. 18 is a cross-sectional view per line 18—18 taken in FIG. 15 showing the device in the passive mode;

FIG. 19 is a view similar to FIG. 18 showing the device in the active mode;

FIG. 20 is a partial, broken away perspective view of the second variation of the second embodiment of the present invention;

FIG. 21 is a full plan view of the device in FIG. 20;

FIG. 22 is a cross-sectional view per line 22—22 taken in FIG. 21;

FIG. 23 is a left end view per line 23—23 taken in FIG. 21;

FIG. 24 is a cross-sectional view per line 24—24 taken in FIG. 21;

FIG. 25 is a right end view per line 25—25 taken in FIG. 21;

FIG. 26 is a cross-sectional view of the third variation of the second embodiment of the present invention.

FIG. 27 is a perspective schematic view of another embodiment of the present invention;

FIG. 28 is an enlarged sectional view thereof taken along line 28—28 in FIG. 27;

FIG. 29 is an enlarged sectional view thereof taken along line 29—29 in FIG. 28;

FIG. 30 is an enlarged sectional view similar to that of FIG. 29, but showing the device in use.

FIG. 31 is a perspective view of a customizable allergen carrier strip according to the present invention;

FIG. 32 is a cross-sectional view thereof taken along line 32—32 in FIG. 31;

FIG. 33 is a perspective view of an allergen package which is receivable in the allergen strip of FIG. 31;

FIG. 34 is a cross-sectional view of the allergen package of FIG. 33 taken along the line 34—34 in FIG. 33;

FIG. 35 is a perspective view of another embodiment of a customizable allergen carrier strip;

FIG. 36 illustrates connecting of two testing devices together with means of a U-shaped connector member; and FIG. 37 illustrates a crown-type needle for use in the present invention.

DETAILED DESCRIPTION

Referring to the drawings, FIG. 1 shows an allergy testing apparatus according to the present invention which comprises four allergy testing sections 100, each of which is identical to the others, and which are interconnected (by means discussed hereinafter) to form a single unitary device. According to a preferred embodiment, as will become apparent from the following discussions, each allergy testing section 100 is capable of performing ten individual allergy tests with ten respective individual allergens. More or fewer than ten simultaneous tests can be performed, as desired, as will become clear from the description hereinbelow. When four identical units 100 are interconnected together as shown in FIG. 1, each unit is arranged to administer ten (in the illustrated embodiment) different allergy tests with ten different respective allergens, so that, in the embodiment of FIG. 1, a total of forty individual allergen tests may be administered simultaneously by the practitioner. The composite unit 110 shown in FIG. 1 has a single actuating member 102 which spans the four sections 100 and engages over the actuating members of each of them (to be described hereinafter) so as to actuate all four of the sections substantially simultaneously.

FIG. 2 shows the apparatus of FIG. 1 in the disassembled state. As can be seen from FIG. 2, each of the sections 100 has respective rod-like protruding members 112 at respective opposite ends thereof. The rod-like protruding members 112 are arranged to be inserted into holes 114 on the other side surfaces of the respective sections 100 so as to frictionally engage in the respective holes 114 to substantially lock two adjacent sections 100 together. As shown in FIG. 1, four adjacent sections 100 are interlocked together in this fashion. Other interlocking techniques could be used.

Each of the sections 100 comprises a frame 116 having opposite side members 118, 120 and opposite end members 122, 124 which are interconnected between the side members 118, 120, to form a substantially box-like member. The rod-like protrusions 112 and holes 114 are formed in respective outwardly extending portions of the side members 118, 120 which extend past the vertical end members 122, 124. The frame 116 is preferably molded as a single unitary member from plastic or other material, and preferably plastics such as acetal, Celcon, Delrin, nylon, or other suitable plastics.

The sections 100 each include a suspended needle carrying actuating member 130 which has an upper finger-engaging portion 132 which is adapted to be pushed by one or more fingers of the operator to actuate the device. As shown in FIGS. 1 and 2, a large actuating member 102 can be installed over members 132 of adjacent sections 100, to simultaneously actuate a number of sections substantially at the same time. Needle carrying member 130 can be made from the same materials as frame 116.

The needle carrying member 130 is suspended from the end walls 122, 124 of the box-like housing 116 by means of flexible, resilient suspension members, for example flexible suspension members 140, as best seen in FIG. 4. Flexible suspension members 140 can be adhered to the respective end walls 122, 124 by means of an adhesive or the like, or can be molded integrally with the end walls 122, 124. Preferably, suspension members 140 are integrally molded with the needle carrying member 130, or, if desired, they can be connected thereto by means of, for example, an adhesive or the like.

FIG. 4A shows an alternate embodiment wherein a suspension member 142 replaces each suspension member 140. The suspension member 142 in FIG. 4A is of tortuous shape and serves as a resilient spring-like flexible suspension member. Suspension member 142 is integrally molded with the needle carrying member 130 and the end wall 124. Similarly, the tortuous shaped suspension member 142 at the opposite end of needle carrying member 130 is integrally molded with needle carrying member 130 and end wall 122. The tortuous shaped suspension members 142 are made of plastics material, like the remainder of the device, and are sufficiently thin so as to serve as resilient spring-like members to bias needle carrying member 130 in the upward position and to permit resilient manual movement of member 130 downwardly against the spring action of suspension members 142. Other suspension devices can be provided, as desired. The advantage of the arrangement shown in FIG. 4A is that a single molding forms not only the outer housing 116 and the needle carrying member 130, but also the flexible suspension means 142 interconnecting them together.

Guide rails or ribs 119 are formed in side wall 118 of the housing 116, and guide rails or ribs 121 are formed in side wall 120 of housing 116. These guide rails or ribs 119, 121 are arranged to reduce the side clearance between needle carrying member 130 and the housing 116 so as to more positively guide the needle carrying member 130 downwardly, preventing pivoting movement or sideways movement thereof, during operation of the device, as will become more apparent from the discussion of operation given in connection with FIGS. 10 and 10A.

The housing 116 has a slot 150 formed at one end thereof for receiving an allergen carrier 160 therein. The slot 150 is defined between a lower portion of the right-side end wall 124 and a base member 126 of housing 116. The left-side end wall 122 extends all the way down to the base 126 of housing 116, as best seen in FIG. 4. Thus, the left end wall 122 serves as a "stop member" for stopping further insertion of allergen carrier 160, and serves to provide proper alignment of allergen carrier 160 in the allergen testing section 100. At the lower edge of each wall 118 and 120 an inward turned track member 127 is used to support allergen carrier 160 for most of its length.

The needle carrying member 130, in the embodiments shown in the drawings, carries ten needles 134 which are integrally molded therein, and which extend out from the lower surface 131 thereof by a predetermined distance, which depends upon the degree of pricking or puncturing or piercing or scratching desired to be carried out on the skin of the patient. More or fewer than ten needles may be provided, and the size of the device in the length direction thereof may be accordingly adjusted in manufacture, depending upon the number of needles used. Various sizes and/or styles of needles can be used, depending upon the type(s) of test(s) to be performed. The needles are preferably made of stainless steel. For example, for intradermal tests, a crown-type needle with multiple needle points such as shown in FIG. 31, could be used. Preferably, the needles 134 are equidistantly arranged along the center line of member 130, as shown in the drawings, so as to be in registration with various allergen sections 161 of allergen carrier 160, as will be explained hereinbelow. As should be readily apparent, the number of allergen sections 161 on the allergy carrier 160 will correspond to the number of needles on the needle carrying member 130. Instead of arranging the needles 134 equidistantly along the length of the needle carrying member 130, the needles could be unequally spaced, as desired for particular tests, and/or the needles could be unequally spaced so as to provide a "marking system" so that the practitioner can easily determine the order of placement of the various substances for which the patient is being tested. That is, by unequally spacing one or more of the needles in needle carrying member 130, the practitioner can easily determine the orientation of the device on the patient, thereby enabling easier determination of the location of particular testing substances on the patient's skin.

Allergen carrier 160 comprises, as best seen in FIG. 11, a central sheet-like support member 162, preferably made of plastic, having apertures 164 therein. A lower sheet 166 of thin, easily pierceable plastic, such as a polyethylene film or the like, is adhered to the lower surface of central support member 162, and an allergen substance 168 is inserted in each aperture 164. The allergen carrier is then covered with an upper layer 170 of thin, easily pierceable plastic, such as a polyethylene film or the like, to seal in the allergen substance 168 retained within the space between the upper and lower layers 166, 170 and retained within the respective aperture 164 of the central support member 162. As seen in FIG. 2, ten openings or apertures 164 are equidistantly (or unequidistantly, as desired) spaced along the allergen carrier 160 so as to provide spaces for ten different allergens 168 in each respective aperture 164, which are in registration with needles 134 when the allergen carrier 160 is inserted into the housing 116, such as shown in the assembled state in FIG. 4. Then, when the actuating member 132 in FIG. 4 is pressed downwardly in the direction of arrow A, the needles 134 pierce the upper and lower film layers 170, 166 of the allergen carrier so as to contact and "pick-up" the respective allergen substance 168 contained in allergen carrier 160, and to thereby apply the picked-up allergen substance to the pricked, scratched or punctured skin of the patient, as shown for example in FIG. 10A.

When the devices of FIGS. 1-12 are not in use, it is preferable to securely and positively maintain the needle carrying member in the "up" position, whereby the needles are maintained recessed within the outer boundaries of the housing, to prevent inadvertent scratching or pricking of the practitioner and/or of the patient. The "up" position is illustrated, for example, in FIG. 4, wherein it is seen that the needles 134 are recessed within the housing. This "up" position can be maintained by various means, for example by inserting a rod-like member 180 into space 182 formed between the needle carrying member 130 and cut-out portion 184 of the housing 100. The space 182 for insertion of the rod 180 is also shown in FIG. 4. When the rod 180 is inserted into the space 182, the needle carrying member 130 is positively prevented from being moved downwardly. The length of the rod 180 is dependent upon the number of needle carrying members which are stacked adjacent each other. While the rod 180 is shown as being round, it could take other cross-sectional shapes to fit and/or to lock within the space 182.

Other means for maintaining the needle carrying member in the "up" position during non-use can be provided. For example, as shown in FIG. 10B, the guide rails or ribs 119, 121 can be provided with small nub-like projections 186 (bumps), and the needle carrying member can be provided with corresponding small nub-like projections (bumps) 188 which engage projections 186 on the respective guide rails 119, 121. Only one such pair of nubs or projections 186, 188 is shown in FIG. 10B, which is an enlarged fragmentary view which is provided for ease of illustration. When the needle carrying member 130 is pressed downwardly in the direction of arrow A (as in FIG. 10A), the projection 188 is resiliently forced over projection 186 when the downward force exceeds a certain threshold value which depends upon the resiliency of the members, the height of the respective bumps or projections, etc. This arrangement maintains the needle carrying member 130 in the "up" position during non-use. The amount of force required to pass bump 188 over bump 186 can be adjusted by varying the sizes of the respective bumps 186, 188, and the clearance between the needle carrying member 130 and the respective guide rails 119, 121. While only one guide rail 121 is shown in FIG. 10B, it should be clear that the pairs of bumps 186, 188 could be provided on as many of the guide rails 119, 121 as desired, for desired operation. As should be apparent other means for maintaining the "up" position of the needles during non-use could be provided, the particular embodiment described above being given by way of example.

By maintaining the needle carrying member 130 in the "up" position during non-use, not only is harm to the practitioner and/or patient insured, but also the needles are prevented from inadvertently contacting the allergens in the respective containers until the actual time of application of the allergen test or the like, thus avoiding possible contamination.

In use, a practitioner, would ordinarily apply a predetermined number of substance tests to the patient, such as allergen tests. Typically, up to forty different allergen or substance tests are applied. This can be accomplished simultaneously using the present invention by stacking four units, each holding ten substances or allergens. If, as a result of the first testing, a group of tests show positive results and a group of tests show negative results, a selective re-test is given, usually at higher doses of application of allergen. The second test is usually an intradermal test. In carrying out the second selective re-testing, it is necessary to customize the combination of substances applied to the skin of the patient. Therefore, according to a further feature of the invention, as shown in FIGS. 31 and 32, a customizable allergen carrier 400 is provided, having recesses or allergen-receiving cavities 402 therein. FIG. 31 is a fragmentary view, the length of the allergen carrier being determined by the length of the device in which it is to be inserted, and the number of allergen-receiving recesses 402 corresponding to the length or the device or number of needles provided in the device in which it is to be used. Only one such allergen receiving opening 402 is shown in FIG. 31 by way of example, it being clear that additional openings can be provided, similar to allergen carrier 160.

As seen in cross-section in FIG. 32, a ledge 404 is provided in recess 402 on which an allergen containing member 410 (see FIG. 33) may be placed. The allergen containing member 410 may comprise a foam member 412 (FIG. 34) with an allergen or other substance impregnated therein or placed thereon, and covered with a cellophane-like film 414 to seal same. The foam member may be a foam-rubber type material and could be made of plastic or other non-allergic foamed material, or any other type of material which will retain an allergen or the like therein or thereon. The allergen carrying members 410 can be chosen at will from many different substances, concentration, dose, etc, so that customized testing can be carried out. The allergens could just be dropped onto a lower pierceable surface of the carrying member 410 and covered over with a pierceable layer to retain the allergen in the carrier.

The practitioner would be provided with a number of different allergen containing or carrying members 410, which could be selectively inserted into openings 402 in a carrier strip 400. This would provide customizing of the second series of tests which are applied to a patient. If a testing device of given length (for example, length of ten needles as shown in drawings) is used, and if it is only desired to give a fewer number of allergen tests, a standard length allergen carrier 400 could be provided, the predetermined number of specific allergen carrying members 410 placed therein. In the blank openings in which no test is to be provided, an insert member similar in shape and size to allergen carrying member 410 could be inserted into the "blank" sections, and could be made of substantially impregnable material (such as Kevlar) to prevent the needle in the empty sections from piercing the skin of the patient. Other types of "blocking" members could be used to prevent the unused needles from piercing the skin of the patient.

Alternatively, devices of different length (different numbers of allergen tests) could be provided to the practitioner. For example, in addition to the "standard" device described herein which provides for ten simultaneous tests (ten needles and associated allergens are provided), smaller devices having, for example, three needles, five needles, seven needles, or the like could be provided, for selective use during the secondary testing process. If such shorter allergen testing devices are provided, then the allergen carrier 400 of FIG. 31 ca be provided with notched or weakened sections 420 shown by dashed lines in FIG. 31 so that the allergen carrier can be "snapped" apart at the weakened sections 420 to customize the length thereof. Therefore, the allergen carriers can be provided in lengths of ten allergen testing spaces, and can be snapped off to make them shorter, as required for the particular device in which they are to be used.

Another customizable allergen carrier 430 is shown in FIG. 35. The allergen carrier 430 comprises a plurality of interlocking sections 432 which interlock with "tongue-and-groove" interlocking members 433. The tongue-and-groove interlocking members extend across the width of the members 432 so that secure interlocking is obtained with a friction fit or with other type of engaging means to lock the members together. Other interengaging means of the allergen carrying sections 432 could be provided. The allergens contained in the allergen sections 432 are shown by way of dashed lines 434, and may be provided in the same manner as in allergen carrier 160 or allergen carrier 400 of FIG. 31.

Another embodiment of the invention is illustrated in FIGS. 13-26 which can be advantageously fabricated from flexible plastic material. Shown in the figures are three variations 250 (FIGS. 13-19), 260 (FIGS. 20-25) and 270 (FIG. 26) where each has an integrally formed housing member comprising a base portion 200 having a lower channel 201 formed therein for receiving an allergen carrier in the form of a strip, such as allergen carrier 160 described hereinbefore. Each housing of device 250, 260 and 270 has an opening 203 (see FIGS. 15 and 22) at one end for receiving the allergen carrier 160 therethrough so that the allergen carrier 160 slides into the channel 201 and is firmly seated in the device. Each device 150, 160 and 270 has an integrally formed spring-like intermediate section 210 and an upper section 220, the spring section 210 being intermediate the top and bottom sections 220, 200 respectively.

As mentioned above, the housing of the device is fabricated as a single unitary member of plastic material by molding, for example, by blow molding. Openings such as slot 203 and bottom port 205 can be formed at molding; machined after molding; cut by "hot knife" tooling or otherwise formed in the housings as required. The plastics material from which the devices are made has sufficient resilience so that the intermediate spring portion 210 will bias the upper portion 220 upwardly in the direction of arrow A, as seen in FIGS. 18, 24 and 26. Each of the devices 250, 260 and 270 is shown to have a set of ten needles 230. As in the case of the previous testing section 10, the number and/or style of needles provided may be varied, with appropriate manufacturing adjustments. For example fewer needles (i.e., for fewer tests), the device could be made shorter.

Device 250 (FIGS. 13-19) contains an upwardly directed hollow protrusion 240 in the upper section 200 to receive a needle carrier strip 241. At assembly, needle carrier strip 241 with needles 230, is passed through lower opening 205 and cemented or otherwise adhered or secured within upward hollow protrusion 240. Strip 241 has a lower surface 242 that comes to bear on the upper surface of the allergen carrier 160 when device 250 is compressed in the "in use" mode as seen in FIG. 19. This "stop" feature allows for the proper penetration or pricking of the patient's skin by needles 230 to apply the various allergens. Openings 164 on allergen strip 160 are arranged to come in registration with needles 230 when carrier 160 stops against wall 243 (FIG. 15). Other types of "stop" means may be provided. For example, projections can be arranged to extend downwardly from the inner upper surface of the housing at opposite ends thereof, so as to abut on the inner lower surfaces of the housing or on the end surfaces of the strip 160 at opposite ends thereof, to limit penetration of the needles 230.

In device 260 there is no protrusion similar to 240 to hold a needle carrier strip 261, but instead, advantage is taken of channel 212 already formed in the housing 260. Needle carrier strip 261 has a modified "T" cross section (FIG. 24) and supports needles 230. On the end of device 260 opposite allergen carrier slot 203, an opening 262 (FIGS. 22 and 23) allows for the insertion of needle carrier strip 261 so that needles 230 are in registration with openings 164 in allergen strip 160. Needle carrier 261 may be press fitted in; cemented to or otherwise adhered or secured or fastened to the housing of device 260. In other respects, device 260 is similar to device 250.

FIG. 26, the third variation 270 of the second embodiment of the present invention, is shown to have no carrier strip to hold needles 230. During the forming of the housing for device 270 (for example during molding or after molding) a wall extension 271 is folded so tightly about needles 230 as to form a rigid member to hold the needles 230 in place. In other respects, the third variation 270 is similar to the first and second variations 250, 260.

The embodiments 250, 260 and 270 of FIGS. 13-26 can be stacked adjacent to each other (similar to members 100 of FIGS. 1 and 2), and a single actuating member (similar to actuator 102 of FIGS. 1 and 2) may be provided over the top of the respective sections. Either the members 250, 260, 270 could have interengaging members thereon, or separate clips could be provided to clip the members together. For example, U-shaped wire clips could be provided at each end of the device so as to engage around two adjacent devices, with the legs of the U-shaped devices being arranged in the inwardly directed apex of the intermediate section 210. If the U-shaped wire connecting members are thin enough, operation will not be adversely affected thereby.

The devices 250, 260, 270 could be provided with weakened or score marks thereon, at which point they could be snapped apart to provide devices of different length, to conduct different allergen tests, as required. In such snapped apart or broken off shortened members, allergen carriers such as shown in FIGS. 31 and/or 35 could be used, to permit administration of the desired substance tests.

FIG. 36 shows a pair of allergen testing members 250 connected adjacent each other by means of a U-shaped wire member 450 the U-shaped member 450 includes a pair of legs 451, 452 and a cross-member 453 interconnecting the legs 451, 452. In FIG. 36, the U-shaped member 450 is inserted from the rear, it being clear that a second one is inserted from the front, so that the two devices 250 are clipped together at both opposite ends thereof. The clips 450 can be made from wire, plastic or the like. The lengths of the legs 451, 452 in the longitudinal direction of the device should be at least sufficient so a to engage over at least 10% of the longitudinal length of the respective devices 250. Other lengths could be used, depending upon the stiffness of the material from which the U-shaped clips are made.

When using the device(s) of the second embodiment, an allergen strip 160 or the like is arranged within channel 201. The lower base portion 202 of the device is then placed against the skin of the patient. The upper portion 220 of the device is then pressed downwardly by hand so that the upper portion 220 moves in the direction of arrow B (see FIGS. 19 and 25) compressing spring section 210. As a result of this action, needles 230 pierce the openings 164 in the strip-like allergen carrier 160, and then proceed downwardly to prick the skin of the patient. The device(s) are so dimensioned as to cause minimum trauma to the patient and yet carry allergen 168 thereto.

FIG. 27 schematically illustrates yet another embodiment 300 of the present invention in a configuration similar to a "roller", the embodiment having a handle 302, a housing 304 and a roller 306 rotatably mounted to an axle 308 in the housing 304. In use, the device is placed on the skin of a patient and is rolled, for example in the direction of the arrow C in FIG. 29, along the skin of the patient so as to apply the allergen tests, as will become apparent from the following description.

FIGS. 28 and 29 illustrate a cross-sectional view of the roller 306 which comprises a rigid core member 310 having an axle-receiving opening 312 in the central portion thereof. Surrounding core member 310 is a cylindrical member 314 having a plurality of needle members 316 projecting therefrom. The needle members 316 are metallic needles which are either attached to or integrally molded to the cylindrical member 314. In the illustrated embodiment, ten needle members 316 are shown. The device further comprises a foam or other resilient layer 320 which preferably completely covers the needles 316, including their tip ends. The resilient layer 320 is preferably formed of a foam rubber or plastic, material, or the like, and the operation thereof will be described hereinbelow.

The next layer comprises an allergen-carrying layer 324 which is generally similar to the strip-like allergen carrier 160 described previously, but is in the form of a cylindrical member. The allergen carrying layer 324 has compartments 326 spaced therearound and in registration with the respective needles 316, for receiving respective allergens therein. The allergen carrier is sealed at the outermost surface and the innermost surface of layer 324 with a thin, pierceable layer, which is pierceable by the needles 316 in use. In use, when the device is placed on the skin of a patient, the device is pressed downwardly in the direction of the arrow D in FIGS. 29 and 30 so as to compress resilient layer 320 to cause the lowermost needle to pierce the allergen containing portion 326 and to then contact the skin of the patient to prick the skin of the patient and to apply the allergen in the respective allergen containing portion 326 to the pricked skin, thereby performing the allergy test on the particular portion of the patient's skin. Then, in use, the device is moved in the direction of the arrow C so as to "roll" along the patient's skin and to successively compress areas of resilient layer 320 in the vicinity of a respective needle which is just above the patient's skin, to thereby apply successive prick tests to the skin of the patient while the device is rolled in the direction of the arrow C. In this manner, in the embodiment illustrated in FIGS. 27-30, the device applies ten prick tests at spaced apart portions along the skin of the patient.

In the embodiment as shown in FIGS. 27-30, the spacing between needles 317 and 318 is greater than the spacing between other respective pairs of adjacent needles, so that the operator of the device can easily determine the relative location of respective needles 317 and 318 (by the larger distance between the "pricks" on the skin of a patient), and can therefore determine the particular type of allergen which was applied, since the allergens are applied to the skin in a predetermined order. In the other illustrated embodiments of the invention, spacing differences can be provided to determine orientation of the device and relative location of the substances, or other marking of the device or skin of the patient could be used.

FIG. 30 illustrates the device of FIGS. 27, 28 and 29 in operative use against the skin of a patient, with the lowermost needle 318 piercing or pricking the skin of a patient and with the layer 320 compressed in the vicinity of the skin of the patient.

The device of FIGS. 27-30 preferably also includes transverse locating projections 340, 342 on the outer surface of core member 310 and on the inner surface of layer 324, respectively. An additional protrusion 344 may be provided on the outer surface of layer 314. Corresponding depressions are provided in the mating portions. These protrusions 340, 342 and 344 insure that the devices are assembled with the proper orientation relative to each other so that the needles are respectively in registration with the particular associated allergen.

As seen in the perspective view of FIG. 27, the device is generally cylindrical. Additional allergen tests can be simultaneously carried out by stacking adjacent sections of the applicator device along the axial direction of the axis 308, with suitable changes in housing 30A, to effect stacking of the devices side-by-side in an appropriate carrier having a handle 302 thereon for easy manipulation by an operator.

Alternatively, the roller 306 can be made wider, and can be provided with two or more circumferential rows of needles 316 and associated allergen carrier layers 324 in registration therewith. In this manner, more allergen tests can be performed simultaneously.

The devices of FIGS. 27-30 can be "customized" to provide selective allergen testing by replacing the allergen carrying layer 324 with either another prefabricated allergen testing layer or a customizable allergen test carrying layer or a customizable carrying layer. The allergen carrying layers 324 can be made customizable in a manner similar to FIG. 31 by providing a plurality of recess 402 therein with associated ledges 404 to retain the allergen testing substance therein. In this arrangement, the lip or ledge 404 would be radially outward of the device so that the wider opening of recess 402 is arranged inwardly of the device against the resilient layer 320. By using such an arrangement, when the allergen carrying members are inserted into the recesses 402, they are retained in position against the resilient layer 320 from the inside, and are retained in position by the ledge 404 from the outside, thereby effectively locking them in place. If desired to carry out fewer tests than the number of needles on the device of FIGS. 27-30, the "empty" or non-testing openings 402 can be filled with a non-pierceable member such as Kevlar or other rigid material which will not be pierced by the needles 316, thereby preventing unnecessary piercing of the skin of the patient.

The needles of the present invention are shown as simple pointed members throughout the drawings. However, any of the needles can be replaced by crown-type needles having a plurality of small of projections at the tip end thereof, as shown in FIG. 37. Such crown-type needles have a shaft portion 460 and a needle portion 462 having a plurality of downwardly extending small needles 463 for piercing through the allergens and then for piercing the skin of the patient. Alternatively, a needle such as shown in U.S. Pat. No. 3,291,129 could be used, or other known needles could be used.

As can be seen from the foregoing discussion, the allergen testing device of the present invention permits quick, easy testing by the practitioner of a patient for sensitivity to a plurality of substances, substantially all at the same time. The test can be predetermined standardized tests, or a practitioner could prepare or order special or custom combinations of substances, as required by the respective practitioner. Also, the strengths and/or concentration of the various substances can be varied, for example by providing the customizable carrier strips, or a plurality of different strength standardized strips could be provided to the practitioner for specific uses. Still further, various devices having different length needles could be provided to enable different types of testing. For example, initial testing of a patient is generally done by a scratch test, which is generally known as epidermal testing. Subsequent tests for sensitivity to specific substances which may have shown positive in the first tests are done by deeper piercing, which is sometimes known as intradermal testing. For the intradermal testing, needles having a slightly longer length could be provided to provide deeper piercing or penetration of the skin of the patient during use. For such intradermal testing, the crown-type needles such as shown in FIG. 37 provide excellent results.

Having described specific preferred embodiments of the invention with reference to the accompanying drawings, it will be appreciated that the present invention is not limited to those precise embodiments and that various changes and modifications can be affected therein by one of ordinary skill in the art without departing from the spirit or scope of the invention, as defined in the appended claims.

We claim:

1. An allergy testing apparatus for testing a patient for a plurality of allergies at substantially the same time, comprising:
    a frame member;
    an actuating member resiliently suspended from said frame member by suspending means;
    actuating means on said actuating member for moving said suspended actuating member relative to said frame member;
    a plurality of spaced apart substance sources mounted in said frame member below said actuating member for carrying respective substances which are to be applied to the skin of a patient for testing; and
    a plurality of spaced apart pricking or piercing means on said actuating member and extending in substantially the same direction, each pricking or piercing means being associated with a respective substance source, said pricking or piercing means being movable from an inactive position out of contact with the skin of a patient to an active position for pricking or piercing the skin of a patient and applying an associated substance from said respective substance source to the skin of the patient when moved from said inactive position to said active position;
    said actuating member being movable relative to said frame member against the resiliency of said resilient suspending means for moving said plurality of pricking or piercing means from said inactive position to said active position to contact said substances contained in said plurality of spaced apart substance sources, respectively, and to apply the respective substances to the pricked or pierced skin of the patient at substantially the same time with said substances being spaced apart on the skin of said patient.

2. The allergy testing apparatus of claim 1, wherein said spaced apart pricking or piercing means comprises a plurality of elongated pricking or piercing members which are fixedly connected to said actuating member.

3. The allergy testing apparatus of claim 2, wherein said pricking or piercing means comprises a plurality of elongated needles.

4. The allergy testing apparatus of claim 1, wherein said plurality of substance sources are arranged in a strip member which is selectively receivable in said frame member, said strip member being separable from said pricking or piercing means.

5. The allergy testing apparatus of claim 4, wherein said strip member comprises an elongated frame, said elongated frame including means for receiving a plurality of spaced apart testing substances therein, said substance carrying means being pierceable by said pricking or piercing elements, whereby said pricking or piercing elements pierce said substance carrying means and contact said respective substances during movement from said inactive to said active position.

6. The allergy testing apparatus of claim 5, wherein said substance carrying strip is adjustable in length.

7. The allergy testing apparatus of claim 1, wherein said suspending means comprises resilient elements coupling said actuating member to said frame member at opposite end portions thereof.

8. The allergy testing apparatus of claim 7, further comprising guide means on at least one of said frame member and said actuating member for guiding said actuating member relative to said frame member during movement of said actuating member from said inactive to said active position.

9. The allergy testing apparatus of claim 8, further comprising means for coupling a plurality of frame members together, each of said frame member comprising respective actuating members, pricking or piercing means and spaced apart substance sources.

10. The allergy testing apparatus of claim 9, further comprising means coupled to said actuating members of said connected together frame members for actuating all of said actuating members substantially at the same time.

11. The allergy testing apparatus of claim 1, further comprising locking means for locking said actuating member in said inactive position to prevent inadvertent movement of said pricking or piercing means from said inactive to said active position.

12. The allergy testing apparatus of claim 1, wherein said frame member completely surrounds said actuating member in the horizontal direction.

13. The allergy testing apparatus of claim 1, wherein said suspending means is interposed between said frame member and said actuating member.

14. The allergy testing apparatus of claim 13, wherein said frame member, said suspending means, and said actuating member are formed as a one-piece unitary structure.

15. The allergy testing apparatus of claim 1, wherein said unitary structure is a single molded unit.

16. The allergy testing apparatus of claim 15, wherein said suspending means comprises a resilient inwardly directed section interposed between said actuating member and said frame member.

17. The allergy testing apparatus of claim 16, wherein said inwardly turned or said inwardly directed suspending means comprises a generally V-shaped portion.

18. The allergy testing apparatus of claim 14, wherein said suspending means comprises a generally V-shaped resilient portion between said frame member and said actuating member.

19. The allergy testing apparatus of claim 14, wherein said plurality of spaced apart pricking or piercing means are mounted directly to said actuating member.

20. The allergy testing apparatus of claim 14, wherein said plurality of spaced apart pricking or piercing means are mounted to an elongated strip-like mounting member which is coupled to said actuating member.

21. The allergy testing apparatus of claim 14, wherein said frame member comprises a lower portion of said unitary structure and comprises an opening for receiving an elongated strip carrying said plurality of spaced apart substance sources.

22. The allergy testing apparatus of claim 21, wherein said lower portion of said unitary structure comprises guide means therein in communication with said opening for receiving and guiding said elongated strip during insertion thereof into said opening.

23. The allergy testing apparatus of claim 16, wherein said frame member, said suspending means and said actuating member are blow molded as a single unitary structure.

24. The allergy testing apparatus of claim 18, further comprising means for interconnecting a plurality of said allergy testing units together.

25. The allergy testing apparatus of claim 24, wherein said interconnecting means comprises means for engaging the generally V-shaped resilient portion of adjacent allergy testing apparatus.

26. The allergy testing apparatus of claim 6, wherein said substance carrying strip comprises a plurality of substance carrying sections interlocked together to form an elongated strip.

27. The allergy testing apparatus of claim 26, wherein said substance carrying strip comprises interlocking means interconnecting said substance carrying sections together.

* * * * *